United States Patent [19]

Fountain et al.

[11] Patent Number: 4,588,578
[45] Date of Patent: May 13, 1986

[54] LIPID VESICLES PREPARED IN A MONOPHASE

[75] Inventors: Michael W. Fountain, Plainsboro; Steven J. Weiss, Heightstown; Mircea C. Popescu, Plainsboro, all of N.J.

[73] Assignee: The Liposome Company, Inc., Princeton, N.J.

[21] Appl. No.: 521,176

[22] Filed: Aug. 8, 1983

[51] Int. Cl.[4] ............... A61K 43/00; A61K 49/00
[52] U.S. Cl. ........................... 424/1.1; 424/9; 436/829; 428/402.2
[58] Field of Search ............ 424/1.1, 9; 436/829; 428/402.2

[56] References Cited

U.S. PATENT DOCUMENTS 4,224,179  9/1980  Schneider ..................... 252/316
4,235,871  11/1980  Papahadjopolous .
4,394,372  7/1983  Taylor .

OTHER PUBLICATIONS

Bangham et al., J. Mol. Biol. 13: 238–252 (1965).
Papahadjopolous and Miller, Biochim. Biophys. Acta 135: 624–638 (1967).
Deamer and Bangham, Biochim. Biophys. Acta 413: 629–634 (1976).
Batzri and Korn, Biochim. Biophys. Acta 298: 1015–1019 (1973).
Szoka and Papahadjopolous, Proc. Nat. Acad. Sci. USA 75: 4194–4198 (1978).

*Primary Examiner*—Christine M. Nucker
*Attorney, Agent, or Firm*—Pennie & Edmonds

[57] ABSTRACT

A process for the preparation in a monophasic solvent system of a new type of lipid vesicles, called monophasic lipid vesicles (MPVs). MPVs can be made to encapsulate one or more bioactive agents. MPVs are stable during storage and can be used in vivo in the treatment of disease.

83 Claims, No Drawings

LIPID VESICLES PREPARED IN A MONOPHASE

FIELD OF THE INVENTION

This invention relates to liposomes and their uses as carriers in delivery systems. More specifically, it discloses a new process for making a new type of lipid vesicle having unique properties which confer special advantages such as increased stability, high percentage of drug entrapment and ability to combine incompatible drugs in the lipid vesicle.

The practice of the present invention is demonstrated herein by way of example for the treatment of *Brucella canis* infection and the treatment of *Salmonella typhirium* infection.

BACKGROUND OF THE INVENTION

Liposomes

Liposomes are completely closed bilayer membranes containing an entrapped aqueous phase. Liposomes may be any variety of unilamellar vesicles (possessing a single membrane bilayer) or multilamellar vesicles (onion-like structures characterized by concentric membrane bilayers, each separated from the next by an aqueous layer).

The original liposome preparation of Bangham et al. (1965, J. Mol. Biol. 13:238–252) involves suspending phospholipids in an organic solvent which is then evaporated to dryness leaving a phospholipid film on the reaction vessel. Then an appropriate amount of aqueous phase is added, the mixture is allowed to "swell", and the resulting liposomes which consist of multilamellar vesicles (hereinafter referred to as MLVs) are dispersed by mechanical means. The structure of the resulting membrane bilayer is such that the hydrophobic (nonpolar) "tails" of the lipid orient toward the center of the bilayer while the hydrophilic (polar) "heads" orient towards the aqueous phase. This technique provides the basis for the development of the small sonicated unilamellar vesicles (hereinafter referred to as SUVs) described by Papahadjapoulos and Miller (1967, Biochim. Biophys. Acta. 135:624–638) and large unilamellar vesicles (hereinafter referred to as LUVs). These "classical liposomes" (MLVs, SUVs and LUVs), however, have a number of drawbacks not the least of which is a low volume of entrapped aqueous space per mole of lipid and a restricted ability to encapsulate large macromolecules.

Efforts to increase the entrapped volume involved first forming inverse micelles or liposome precursors, i.e., vesicles containing an aqueous phase surrounded by a monolayer of lipid molecules oriented so that the polar head groups are directed towards the aqueous phase. Liposome precursors are formed by adding the aqueous solution to be entrapped to a solution of polar lipid in an organic solvent and sonicating. The organic solvent is then evaporated in the presence of excess lipid. The resultant liposomes, consisting of an aqueous phase entrapped by a lipid bilayer are dispersed in an aqueous phase (see U.S. Pat. No. 4,224,179 issued Sept. 23, 1980 to Schneider).

In another attempt to maximize the efficiency of entrapment, Papahaduopoulos (U.S. Pat. No. 4,235,871 issued Nov. 25, 1980) describes a "reverse-phase evaporation process" for making oligolamellar lipid vesicles also known as reverse-phase evaporation vesicles (hereinafter referred to as REVs). According to this procedure, the aqueous material to be entrapped is added to a mixture of polar lipid in an organic solvent. Then a homogeneous water-in-oil type of emulsion is formed and the organic solvent is evaporated until a gel is formed. The gel is then converted to a suspension by dispersing the gel-like mixture in an aqueous media. The REVs produced consist mostly of unilamellar vesicles and some oligolamellar vesicles which are characterized by only a few concentric bilayers with a large internal aqueous space. Certain permeability properties of REVs were reported to be similar to those of MLVs and SUVs (see Szoka and Papahadjopoulos, 1978, Proc. Natl. Acad. Sci. U.S.A. 75:4194–4198).

Batzri and Korn (1973, Biochim.Biophys. Acta. 298:1015–1019) describe a process for the preparation of liposomes by an ethanol-infusion method. This method yields SUVs which have to be separated from a carrier liquid and then resuspended in an aqueous phase. All procedures used to effect this have been uneconomical. Furthermore, the SUVs produced are unstable. Additional disadvantages of this method are that it produces liposomes with a low entrapment efficiency and it is limited to using lipids which are soluble in ethanol.

Liposomes which entrap a variety of compounds can be prepared; however, stability of the liposomes during storage is invariably limited. This loss in stability results in leakage of the entrapped compound from the liposomes into the surrounding media, and can also result in contamination of the liposome contents by permeation of materials from the surrounding media into the liposome itself. As a result the storage life of classical liposomes is very limited. Attempts to improve stability involved incorporating into the liposome membrane certain substances (hereinafter called stabilizers) which affect the physical properties of the lipid bilayers (e.g., steroid groups). However, many of these substances are relatively expensive and the production of such liposomes is not cost-effective.

In addition to the storage problems of classical liposomes a number of compounds cannot be incorporated into these vesicles. For example, MLVs can only be prepared under conditions above the phase-transition temperature of the lipid membrane. This precludes the incorporation of heat labile molecules within liposomes that are composed of phospholipids which exhibit desirable properties but possess long and highly saturated side chains.

Uses of Liposomes

Much has been written regarding the possibilities of using liposomes for drug delivery systems. In a liposome drug delivery system the medicament is entrapped during liposome formation and then administered to the patient to be treated. Typical of such disclosures are U.S. Pat. No. 3,993,754 issued on Nov. 23, 1976, to Rahman and Cerny, and U.S. Pat. No. 4,145,410 issued on Mar. 20, 1979, to Sears, U.S. Pat. No. 4,235,871 issued Nov. 25, 1980, to Papahadjopoulos and Szoka and U.S. Pat. No. 4,224,179, , issued Sept. 23, 1980 to Schneider.

Desirable features of drug delivery systems depend upon the condition being treated. For example, when treating conditions which require maintenance doses of medication, resistance to rapid clearance of the drug accompanied by a sustained release of the drug which will prolong the drug's action increases the effectiveness of the drug and allows the use of fewer administrations. However, if one is treating an intracellular infection, the maintenance of stability in biological fluids, until the point that the liposome is internalized by the infected cell, is critical as is release of the liposome entrapped drug in its bio-active form. Some of the problems encountered in using liposome preparations in vivo include the following:

(1) Liposome-entrapped materials leak when the liposomes are in contact with body fluids. This has been attributed to the removal of the liposomal phospholipids by plasma high density lipoproteins (HDLs), or to the degradation of the liposome membrane by phospholipases, among other reasons. A result of the degradation of the liposomes in vivo is that almost all the liposomal contents are released in a short period of time, therefore, sustained release and resistance of the drug to clearance are not achieved.

(2) On the other hand, if a very stable liposome is used in vivo (i.e., liposomes which do not leak when in contact with body fluids in vivo or in vitro), then the liposomal contents will not be released as needed. As a result, these stable liposomes are ineffective as carriers of therapeutic substances in vivo because the sustained release or the ability to release the liposomal contents when necessary is not accomplished.

(3) Liposomes are internalized by the phagocytic cells of the reticuloendothelial system (RES), and, therefore, are cleared from the system rapidly, rendering the entrapped drug largely ineffective against diseases involving cells other than the RES. On the other hand, because cells of the RES phagocytose liposomes, liposome entrapped drugs may be very useful in treating intracellular infections of the RES. However, after phagocytosis, the liposomal contents are packaged within lysosomes of the phagocytic cell and very often the degradative enzymes contained within the lysosome will degrade the entrapped compound or render the compound inactive by altering its structure or modifying the compound at its active site.

(4) The liposome carriers normally used in delivery systems are expensive and production is not cost-effective. For example, an improved method for the chemotherapy of leishmanial infections using liposome encapsulated anti-leishmanial drugs has been reported by Steck and Alving in U.S. Pat. No. 4,186,183 issued on Jan. 29, 1980. The liposomes used in the chemotherapy contained a number of stabilizers which increased the stability of the liposomes in vivo. However, as previously mentioned, these stabilizers are expensive and the production of liposomes containing these stabilizers is not cost-effective.

(5) Ultimately, the problem encountered in the use of liposomes as carriers in drug delivery systems is the inability to effect a cure of the disease being treated. In addition to rapid clearance and degradation of the entrapped compound, a number of other explanations for the inability to cure diseases are possible. For instance, the liposomes may not deliver a dose which is effective due to the low percentage of entrapment of active compound into the vesicles when prepared.

Liposomes have been used by researchers as model membrane systems and have been employed as the "target cell" in complement-mediated immunoassays. However, when used in such assays, it is important that the liposome membrane does not leak when incubated in sera because these assays measure the release of the liposome contents as a function of serum complement activation by immune complex formation involving certain immunoglobulin classes (e.g., IgM and certain IgG molecules).

SUMMARY OF THE INVENTION

This invention presents a new and improved method of preparation of a new type of lipid vesicle prepared in a monophasic solvent system, which hereinafter will be referred to as monophasic vesicles (MPVs). These vesicles are different from other lipid vesicles in that MPVs possess unique properties when compared to multilamellar vesicles (MLVs), sonicated unilamellar vesicles (SUVs), large unilamellar vesicles (LUVs) and reverse phase evaporation vesicles (REVs). As a result of these differences, MPVs overcome many of the problems presented by classical liposomes heretofore available.

Advantages of the present process include: the use of less toxic solvents for the preparation of the liposome; the ability to incorporate incompatible drugs in the lipid vesicles; the appropriateness for injection; and the reduced possibility of a health hazard to workers.

The properties of MPVs include: (1) the ability to cure certain diseases which other methodologies cannot cure; (2) greatly increased stability of the MPVs over classical liposomes during storage in buffer; (3) the increased ability of MPVs to withstand physiologic environments; (4) the entrapment of materials at high efficiency both in the drying and the rehydration step; and (5) the release of compounds in their bioactive form.

Methods for preparing MPVs, and for the use of MPVs for the delivery of bioactive compounds in vivo and in the treatment of pathologies, such as infections, are described.

DETAILED DESCRIPTION OF THE INVENTION

Preparation of MPV

MPVs are lipid vesicles possessing a plurality of bilayers. The membrane bilayer is composed of a bimolecular layer of an amphipathic lipid in which the nonpolar hydrophobic hydrocarbon "tails" point inward towards the center of the bilayer and the polar, hydrophilic "heads" point towards the aqueous phase. Occluded by the bilayers is an aqueous compartment, part of which makes up the lumen of the vesicle, and part of which lies between adjacent layers. Complexed with the lipid bilayers can be a variety of proteins, glycoproteins, glycolipids, polysaccharides, and any other hydrophobic and/or amphipathic substance.

MPVs are prepared by a unique process as follows: a lipid or a mixture of lipids and an aqueous component are added to an organic solvent or a combination of organic solvents in amounts sufficient to form a monophase. The solvent or solvents are evaporated until a film forms. Then an appropriate amount of aqueous component is added, and the film is resuspended and agitated in order to form the MPVs.

The organic solvent or combination of solvents used in the process must be miscible with water and once mixed with water should solubilize the lipids used to make the MPVs.

For example, an organic solvent or mixture of solvents which satifies the following criteria may be used in the process: (1) 5 ml of the organic solvent forms a monophase with 0.2 ml of aqueous component and (2) the lipid or mixture of lipids is soluble in the monophase.

Solvents which may be used in the process of the present invention include but are not limited to ethanol, acetone, 2-propanol, methanol, tetrahydrofuran, glyme, dioxane, pyridine, diglyme, 1-methyl-2-pyrrolidone, butanol-2, butanol-1, isoamyl alcohol, isopropanol, 2-methoxyethanol, or a combination of chlorform:methanol (e.g., in a 1:1 ratio).

According to the present invention the evaporation should be accomplished at suitable temperatures and pressures which maintain the monophase and facilitate the evaporation of the solvents. In fact, the temperatures and pressures chosen are not dependent upon the phase-transition temperature of the lipid used to form the MPVs. The advantage of this latter point is that heat labile products which have desirable properties can be incorporated in MPVs prepared from phospholipids such as distearoylphosphatidylcholine, which can be formed into conventional liposomes only at temperatures above the phase-transition temperature of the phospholipids. The process usually allows more than 30–40% of the available water-soluble material to be entrapped during evaporation and 2–15% of the available water-soluble material to be entrapped during the resuspension; and up to 70–80% of the available lipid-soluble material can be if the lipid:drug ratio is increased significantly. With MLVs the entrapment of aqueous phase, which only occurs during the rehydration step since no aqueous phase is present during the drying step, usually does not exceed 10%.

Most amphipathic lipids may be constituents of MPVs. Suitable hydrophilic groups include but are not limited to: phosphato, carboxylic, sulphato and amino groups. Suitable hydrophobic groups include but are not limited to: saturated and unsaturated aliphatic hydrocarbon groups and aliphatic hydrocarbon groups substituted by at least one aromatic and/or cycloaliphatic group. The preferred amphipathic compounds are phospholipids and closely related chemical structures.

Specific examples of suitable lipids useful in the production of MPVs are phospholipids which include but are not limited to the natural lecithins or phosphatidylcholines (e.g., egg lecithin or soybean lecithin) and synthetic lecithins, such as saturated synthetic lecithins (e.g., dimyristoylphosphatidylcholine or dipalmitoylphosphatidylcholine or distearoylphosphatidylcholine) and unsaturated synthetic lecithins (e.g., dioleoylphosphatidylcholine or dilinoleoylphosphatidylcholine). Other phospholipids include but are not limited to phosphatidylethonolamine, lysolecithin, lysophosphatidylethanolamine, phosphatidylserine, phosphatidylinositol, sphingomyelin, cardiolipin, phosphatidic acid, ceramides and the cerebrosides. The MPV bilayers can contain a steroid component such as cholesterol, coprostanol, cholestanol, cholestane and the like. When using compounds with acidic hydrophilic groups (phosphato, sulfato, etc.) the obtained MPVs will be anionic; with basic groups such as amino, cationic liposomes will be obtained.

MPVs may advantageously be used in delivery systems wherein a bioactive agent is entrapped within the MPV ("entrapped" is defined as entrapment within the aqueous compartment or within the membrane bilayer). In order to entrap one or more agents in MPVs, the agent or agents may be added to the monophase prior to evaporation and formation of the film. Alternatively, the agent or agents may be added with the aqueous component used to resuspend the film and form the MPVs. In fact, to obtain a high entrapment efficiency, the agent or agents may be added to both the monophase and to the aqueous component used to resuspend the film. Two or more agents can also be entrapped in one MPV preparation by adding one agent to the monophase and the other to the aqueous component used to resuspend the film.

Virtually any bioactive compound can be entrapped within an MPV. Such compounds include but are not limited to: nucleic acids, polynucleotides, antibacterial compounds, antiviral compounds, antifungal compounds, anti-parasitic compounds, tumoricidal compounds, proteins, toxins, enzymes, hormones, neurotransmitters, glycoproteins, immunoglobulins, immunomodulators, dyes, radiolabels, radio-opaque compounds, fluorescent compounds, polysaccharides, cell receptor binding molecules, anti-inflammatories, anti-glaucomic agents, mydriatic compounds, anesthetics, etc.

Also suitable for entrapment are combinations of incompatible drugs. Concurrent therapy with certain antimicrobial agents can be complicated because some agents which are particularly effective when used together in vitro cannot be formulated in a single mixture at therapeutic concentration for use in vivo due to a number of constraints. For example, mixtures of gentamicin and nafcillin at therapeutic concentrations result in the formation of complexes that precipitate out of solution and, therefore, are not administered in vivo simultaneously. In fact, certain drug combinations are not recommended for use in vivo due to drug incompatibility (i.e., either inactivation of the drug or formation of a precipitate). For example, it has been recommended that the following antibiotics not be mixed with any other drug: gentamicin, kanamycin, lincomycin, cephalothin, and ampicillin (Davis and Abbitt, 1977, JAVMA 170(2): 204–207). Moreover, certain agents cannot be solubilized in the same medium due to chemical restraints (e.g., a lipid soluble compound and a water soluble compound). These limitations reduce the possible combinations of agents that may be used to obtain enhancement of biological activity in combined therapy. For a review of the topic see Goodman and Gilman, 1980, *The Pharmacological Basis of Therapeutics* Sixth Edition, pp. 1080–1106 and Davis et al., 1980, Microbiology, pp. 574–583. However, as seen from Examples, infra, incompatible drugs (i.e., nafcillin and gentamicin) can be combined in MPVs to yield concurrent therapeutic results.

The following is an illustrative example of the proportions that may be used in MPV synthesis: MPVs may be formed by adding 127 micromoles of phospholipid to 5 ml of ethanol and then adding 0.2 ml of aqueous component containing the active substance to be encapsulated. The resultant solution which comprises the material to be entrapped and the entrapping lipid is sonicated (sonication is an optional step) while streaming an inert gas over the mixture, thus removing most of the solvent and forming a film. To the resulting film is added 5–10 ml of aqueous component. The resuspended film is agitated in order to produce stable MPVs.

Characterization of MPVs

MPVs are clearly distinct in their properties from liposomes with a single or several lamellae (e.g., SUVs, MLVs and REVs). They have some physical properties in common with lipid vesicles referred to as stable plurilamellar vesicles (SPLVs). SPLVs are described in U.S.

patent application Ser. No. 476,496, filed Mar. 24, 1983, which is herein incorporated by reference. SPLVs are prepared as follows: an amphipathic lipid or mixture of lipids is dissolved in an organic solvent to which are added an aqueous phase and the active ingredient to be entrapped. The aqueous material is emulsified into the solvent while the solvent is being evaporated. The resulting lipid vesicles exhibit increased stability in storage and greater medicament entrapment capacity than classical liposomes.

MPVs exhibit greater stability in urea than do SPLVs. The following detailed comparison is focused on distinguishing MPVs from SPLVs and MLVs.

Stability of MPVs in storage

Stability of a lipid vesicle refers to the ability of the vesicle to sequester its occluded space from the external environment over a long period of time. For a lipid vesicle to be useful it is paramount that it be stable in storage and handling. For some applications, however, it is desirable that the vesicle leak its contents slowly when applied. For other applications it is desirable that the vesicle remain intact after administration until it reaches its desired site of action. It will be seen that MPVs demonstrate many of these desirable characteristics.

There are two factors that cause vesicles to leak during storage. One is auto-oxidation of the lipids whereby the hydrocarbon chains form peroxides which destabilize the bilayers. Vesicles can also leak because agents in the exterior environment disrupt the bilayer organization of the lipids such that the lipids remain intact, but the membrane develops a pore.

In the following experiments vesicles were prepared which contained radioactive tracer molecules within the occluded aqueous compartments. When placed in a buffer containing isotonic saline at neutral pH, MPVs containing antibiotic exhibit prolonged stability in storage. The vesicles were prepared, each containing one of the following radio-labeled drugs: $^{125}$I-p-hydroxypropionic acid-derived gentamicin sulfate, $^{14}$C-indomethacin, and $^{3}$H-inulin. After storage at various temperatures for 14 days the vesicles were separated from the medium by centrifugation, and the relative amount of radioactivity that escaped from the vesicles into the medium was determined. The results demonstrated that both MPVs and SPLVs were more stable during storage than were MLVs.

The shelf-life of an MPV preparation can be considerably lengthened by storing the dried film containing the lipids and agent to be entrapped. When fully formed MPVs are desired, the dried film can be resuspended by adding an appropriate amount of aqueous component (e.g., buffer) and agitating the resuspension.

Stability of MPVs in other environments

Placing lipid vesicles in a medium which contains membrane perturbing agents is a way to probe different molecular organizations. Depending on how the membrane is organized, different vesicles will respond differently to such agents.

In the following experiments vesicles were prepared which contained a radioactive tracer molecule ($^{3}$H-inulin) within the occluded aqueous compartment. Inulin, a polysaccharide, partitions into the aqueous phase, and thus when radiolabeled may be used to trace the aqueous contents of lipid vesicles. After an appropriate interval of exposure to a given agent, the vesicles were separated from the medium by centrifugation, and the relative amount of radioactivity that escaped from the vesicles into the medium was determined. These results are reported in Table I.

MPVs respond differently than SPLVs when exposed to urea. Urea is a molecule with both a chaotropic effect (disrupts the structure of water) and a strong dipole moment. It is observed that SPLVs are far more susceptible to urea than MPVs. (See Table I).

TABLE I
STABILITY OF LIPID VESICLES IN 1 MOLAR UREA

| | % Leakage[a] | | |
|---|---|---|---|
| | 1 hour | 3 hours | 5 hours |
| MPVs | 8.3 | 4.9 | 10.8 |
| SPLVs | 4.4 | 29.7 | 49.7 |

[a]Values are expressed as percent leaked, meaning the proportion of radioactive material in the surrounding medium (cpm) relative to the starting amount encapsulated in the vesicles (cpm).

Entrapment of active material by MPVs

MPVs were prepared to which the radioactive tracer molecules were added prior to the drying step. The MPV entrapment efficiency of the biologically active compounds was compared to that of SPLVs prepared with the same components. The vesicles were separated from the suspending preparation medium by centrifugation, and the relative amount of radioactivity retained by the vesicles was determined. These results are reported in Table II.

TABLE II
COMPARISON OF SPLVs AND MPVs

| | % Available Material Entrapped In Aqueous Phase[a] | |
|---|---|---|
| Encapsulation of: | SPLVs | MPVs[b] |
| $^{125}$I—Gentamicin | 32.8 | 38.3 |
| $^{3}$H—Inulin | 36.8 | 36.7 |
| $^{14}$C—Indomethacin | 21.9 | 15.3 |

[a]Values are expressed as percent entrapped meaning the proportion of radioactive material in the liposome pellet (cpm) relative to the starting amount (cpm) added to the preparation.
[b]Radiolabeled material to be entrapped was added to the monophase. After evaporation to a film and resuspension with aqueous buffer to form MPVs, the preparation was pelleted and the radioactivity of the supernatant was determined.

MPVs have similar superiority over traditional MLVs as do SPLVs in the percentage of entrapment of biologically active material. This affords the benefit of conserving material.

Uses of MPVs

MPVs are particularly useful in systems where the following factors are important: stability during storage and contact with body fluids; a relatively high degree of encapsulation. Therefore, MPVs may be used to enhance the therapeutic efficacy of medications; to cure infections; to enhance topical drug delivery; for the production of vaccines; or as diagnostic reagents for clinical tests following release of entrapped "reporter" molecules. The MPVs can also be employed to encapsulate cosmetic preparations, pesticides, compounds for sustained slow release to effect the growth of plants and the like.

The methods which follow, while described in terms of the use of MPVs, contemplate the use of MPVs or any other liposome or lipid vesicle having functional characteristics similar to those of MPVs.

Delivery of bioactive compounds

Delivery of compounds to cells in vitro (e.g., animal cells, plant cells, protists, etc.) generally requires the addition of the MPVs containing the compound to the cells in culture. In one scheme MPVs and SPLVs containing gentamicin were plated onto lawns of *Staphylococcus aureus* and *Salmonella typhimurium* (See Table III). The results demonstrate that MPVs have drug delivery properties similar to SPLVs.

TABLE III

| | ZONES OF INHIBITION[a] | |
|---|---|---|
| | Staphylococcus aureus | Salmonella typhimurium |
| SPLV | 0.29 cm | 0.58 cm |
| MPV | 0.36 cm | 0.82 cm |

[a]Liposomes were prepared as previously described and 10 microliter aliquots were plated onto the lawns as indicated. Zones of inhibition were measured after 24 hours.

MPVs can also be used to deliver compounds in animals (including man), plants and protists. Depending upon the purpose of delivery, the MPVs may be administered by a number of routes: in man and animals this includes but is not limited to injection (e.g., intravenous, intraperitoneal, intramuscular, subcutaneous, intraarticular, intraauricular, intramammary, intraurethrally, etc.), topical application (e.g., on afflicted areas), and by absorption through epithelial or mucocutaneous linings (e.g., ocular epithelia, oral mucosa, rectal and vaginal epithelial linings, respiratory tract linings, nasopharyngeal mucosa, intestinal mucosa, etc.); in plants and protists this includes but is not limited to direct application to organism, dispersion in the organism's habitat, addition to the surrounding environment or surrounding water, etc.

The mode of application may also determine the sites and cells in the organism to which the compound will be delivered. Delivery to the circulatory system (and hence reticuloendothelial cells), may be most easily accomplished by intravenous or intraperitoneal injections.

The sections which follow describe some overall schemes in which MPVs may be used and demonstrate, but do not limit, the scope of the present invention.

Treatment of pathologies

A number of pathological conditions which occur in man, animals and plants may be treated effectively by encapsulating the appropriate compound or compounds in MPVs. These pathologic conditions include but are not limited to infections (intracellular and extracellular), cysts, tumors and tumor cells, allergies, etc.

Many strategies are possible for using MPVs in the treatment of such pathologies; in one scheme, MPVs are used to deliver therapeutic agents to sites of intracellular infections. Certain diseases involve an infection of cells of the reticuloendothelical system, e.g., brucellosis. These intracellular infections are difficult to cure for a number of reasons: (1) because the infectious organisms reside within the cells of the reticuloendothelial system, they are sequestered from circulating therapeutic agents which cannot cross the cell membrane in therapeutically sufficient concentrations, and, therefore, are highly resistant to treatment; (2) often the administration of toxic levels of therapeutic agents are required in order to combat such infections; and (3) the treatment has to be completely effective because any residual infection after treatment can reinfect the host organism or can be transmitted to other hosts.

According to one mode of the present invention, MPVs containing an appropriate biologically active compound are administered (preferably intraperitoneally or intravenously) to the host organism or potential host organism (e.g., in animal herds, the uninfected animals as well as infected animals may be treated). Since phagocytic cells internalize MPVs, the administration of an MPV-encapsulated substance that is biologically active against the infecting organism will result in directing the bioactive substance to the site of infection. Thus, the method of the present invention may be used to eliminate infection caused by a variety of microorganisms, bacteria, parasites, fungi, mycoplasmas, and viruses, including but not limited to: Brucella spp., Mycobacterium spp., Salmonella spp., Listeria spp., Francisella spp., Histoplasma spp., Corynebacterium spp., Coccidiodes spp. and lymphocytic choriomeningitis virus.

The therapeutic agent selected will depend upon the organism causing the infection. For instance, bacterial infections may be eliminated by encapsulating an antibiotic or combination of antibiotics. The antibiotic can be contained within the aqueous fluid of the MPV and/or inserted into the vesicle bilayer. Suitable antibiotics include but are not limited to: penicillin, ampicillin, hetacillin, carbencillin, tetracycline, tetracycline hydrochloride, oxytetracycline hydrochloride, chlortetracycline hydrochloride, 7-chloro-6-dimethyltetracycline, doxycycline monohydrate, methacycline hydrochloride, minocycline hydrochloride, rolitetracycline, dihydrostreptomycin, streptomycin, gentamicin, kanamycin, neomycin, erythromycin, carbomycin, oleandomycin, troleandomycin, Polymyxin B collistin, cephalothin sodium, cephaloridine, cephaloglycin dihydrate, and cephalexin monohydrate.

We have demonstrated the effectiveness of such treatments in curing brucellosis and salmonellosis (see Examples, infra). By the procedure of this invention, the effectiveness and duration of action are prolonged. This system is effective for treating infections which do not respond to known treatments such as antibiotics entrapped in MLVs.

Of course, the invention is not limited to treatment of intracellular infections. The MPVs can be directed to a variety of sites of infection whether intracellular or extracellular.

MPVs are also useful in the treatment of any affliction requiring prolonged contact with the active treating substance. For example, glaucoma is a disorder characterized by a gradual rise in intraocular pressure causing progressive loss of peripheral vision, and, when uncontrolled, loss of central vision and ultimate blindness. Drugs used in the treatment of glaucoma may be applied topically as eyedrops. However, in some cases treatment requires administering drops every 15 minutes due to the rapid clearing of the drug from the eye socket. If an affliction such as glaucoma is to be treated by this invention therapeutic substances such as pilocarpine, Floropryl, physostigmine, carcholin, acetazolamide, ethozolamide, dichlorphenamide, carbachol, demecarium bromide, diisopropylphosphofluoridate, ecothioplate iodide, physostigmine, or neostigmine, etc. can be entrapped within MPVs which are then applied to the affected eye.

Other agents which may be encapsulated in MPVs and applied topically include but are not limited to:

mydriatics (e.g., epinephrine, phenylepinephrine, hydroxy amphetamine, ephedrine, atropine, homatropine, scopolamine, cyclopentolate, tropicamide, encatropine, etc.); local anesthetics; antiviral agents (e.g., idoxuridine, adenine arabinoside, etc.); antimycotic agents (e.g., amphoteracin B, natamycin, pimaricin, flucytosine, nystantin, thimerosal, sulfamerazine, thiobendazole, tolnaftate, grisiofulvin, etc.); antiparasitic agents (e.g., sulfonamides, pyrimethamine, clindamycin, etc.); and anti-inflammatory agents (e.g., corticosteriods such as ACTH, hydrocortisone, prednisone, medrysone, beta methasone, dexamethasone, fluoromethalone, triamcinalone, etc.).

EXAMPLE

Preparation of MPVs

In the subsections which follow, MPVs were prepared by solubilizing a phospholipid in ethanol or other appropriate solvent, adding an aqueous phase and the material to be entrapped, sonicating the mixture at 54° C. while drying under nitrogen until a film formed. The film containing both the lipid and the material to be entrapped was resuspended in an aqueous buffer and agitated in order to form the MPVs.

MPVs containing tetracyclines

A sample containing 127 micromoles of egg phosphatidylcholine (EPC) in chloroform was taken to dryness in a round bottom flask. A 5 ml aliquot of ethanol was added to the flask to resuspend the lipid. A solution (0.5 ml) containing 100 mg of doxycycline monohydrate at approximately pH 7 in physiologic saline was pipetted into the glass vessel containing the ethanol solution of lipid. The monophase was placed in a bath sonicator type 10536 (Laboratories Supplies Co., Inc.) for several minutes, (80 kHz frequency; output 80 watts), at 54° C., while being dried to a film by passing thereover a gentle stream of nitrogen.

To the film remaining 0.3–10.0 ml of physiologic saline was added and the mixture was vortexed while being dried under nitrogen in order to suspend the film and form the MPVs. The preparation was centrifuged at 10,000×g for 10 minutes to remove the non-entrapped doxycycline. This wash was repeated three times. The resulting pellet was suspended in 10 ml of physiologic saline.

The same procedure was used to prepare MPVs containing tetracycline by substituting tetracycline for doxycycline.

MPVs containing gentamicin and nafcillin

MVPs containing both gentamicin and nafcillin were prepared as described above with the following modifications: a 5 ml ethanol solution containing 100 mg EPC was prepared and the following two solutions were added to the lipid-ethanol solution simultaneously: 100 mg gentamicin sulfate in 0.15 ml PBS (phosphate buffered saline) and 100 mg nafcillin in 0.15 ml PBS. The mixture was evaporated at 54° C. and the MPVs were formed as described above.

MPVs containing gentamicin (without nafcillin) were prepared by the same procedure except that 200 mg gentamycin sulfate in 0.3 ml PBS was added to the 5 ml ethanol-EPC solution.

MPVs containing chloramphenicol

MPVs containing chloramphenicol were prepared as described in Section 5.1. except that chloramphenicol (crystalline) was substituted for doxycycline.

Alternate methods of preparing MPVs

MPVs were prepared as follows: 127 micromoles of EPC in chloroform was taken to dryness by rotoevaporation. The lipid was resuspended in 5 ml of ethanol and to this was added 0.2 ml water containing $^3$H-inulin. The resulting preparation was treated as follows to examine the entrapment efficiency of the resulting liposomes:

(1) Vortexing the preparation while drying under nitrogen;
(2) Hand-shaking the preparation while drying under nitrogen;
(3) Drying under nitrogen with no concurrent agitation;
(4) Rotoevaporating under vacuum with no agitation;
(5) Sonicating while drying under nitrogen.

All techniques were carried out at a temperature range of between 50°–60° C. To the dried preparations were added 10 ml of water containing $^{14}$C-sucrose. All preparations were centrifuged at 10,000×g for 10 minutes with three washes.

Final entrapment was determined by liquid scintillation counting techniques using double channel counting. Values expressed as percent entrapment means the percentage of radioactive material in the pelleted liposomes (cpm) relative to the initial amount of radioactive material in the preparation (cpm). The results are shown in Table IV.

TABLE IV

EFFICIENCY OF ENTRAPMENT IN MPVs MADE BY ALTERNATIVE METHODS

| Procedure | % ENTRAPMENT[a] | |
|---|---|---|
| | $^3$H—Inulin | $^{14}$C—Sucrose |
| (1) Vortexing while drying under nitrogen | 31.0 | 2.3 |
| (2) Hand-shaking while drying under nitrogen | 29.7 | 2.4 |
| (3) Stationary drying under nitrogen | 32.6 | 2.2 |
| (4) Rotoevaporation | 32.2 | 2.2 |
| (5) Sonicating while drying under nitrogen[b] | 44.5 | 2.4 |

[a]FIGS. presented represent percent entrapment of the starting volumes used.
[b]Preferred embodiment.

EXAMPLE

Preparation of MPVs using various solvent systems

Choice of solvent system

The following example shows the entrapment efficiency of MPVs that are prepared in different solvent systems. The criteria used for the evaluation of the solvents tested in this example were the following: (1) 5 ml of the organic solvent must form a monophasic solution with 0.2 ml aqueous solvent and (2) EPC must be soluble in the monophase. Of course if less lipid is used to make the MPVs the volumes used in the test would be adjusted accordingly.

Seven organic solvents were evaluated according to the above criteria and the results are shown in Table V.

TABLE V
SELECTION OF SOLVENTS

| Solvent | Criterion 1<br>5 ml of solvent<br>are miscible with<br>0.2 ml H$_2$O | Criterion 2<br>At 50°–60° C.,<br>solvent, lipid and<br>H$_2$O are miscible |
| --- | --- | --- |
| Ethanol | Yes | Yes |
| Acetone | Yes | Yes |
| Dimethylformamide | Yes | No |
| DMSO | Yes | No |
| Acetonitrile | No | Not Done |
| 2-Propanol | Yes | Yes |
| Methanol | Yes | Yes |

These results indicate that four of the solvents examined are suitable to use as solvent for preparation of MPVs. The following example sets forth entrapment efficiency.

Entrapment efficiency of various solvent systems

A sample of 127 micromoles of EPC in chloroform was rotoevaporated to dryness in a round bottom flask, then resuspended in one of the following organic solvents: ethanol, acetone, 2-propanol, or methanol. To this preparation was added 0.2 ml of an aqueous phase containing $^3$H-inulin. This monophase was sonicated at 50°–60° C., and dried under nitrogen. The resulting film was resuspended in 10 ml of water containing $^{14}$C-sucrose after being subjected to centrifugation three times at 10,000×g. Final entrapment of $^3$H-inulin and $^{14}$C-sucrose were determined by dual channel liquid scintillation technique (Dual Beckman LS 6800). The results are shown in Table VI.

TABLE VI
ENTRAPMENT EFFICIENCIES OF VARIOUS SOLVENT SYSTEMS

| Organic Solvent | % ENTRAPMENT[a] | |
| --- | --- | --- |
| | $^3$H—Inulin[b] | $^{14}$C—Sucrose[c] |
| Ethanol | 45.8 | 2.8 |
| Acetone | 38.3 | 2.3 |
| 2-Propanol | 23.7 | 1.3 |
| Methanol | 44.5 | 2.4 |

[a]Values are expressed as percent entrapped meaning the proportion of radioactive material in the pelleted liposomes (cpm) relative to the starting amount of radioactive material (cpm) added to the preparation.
[b]Added to the monophase.
[c]Added to the aqueous resuspension buffer.

EXAMPLE

Treatment of intracellular infections

The following examples demonstrate how MPVs can be used in treating intracellular infections. The data presented demonstrates: (1) the effectiveness of using antibiotics encapsulated in MPVs in the treatment of disease and (2) the greater efficiency which is obtained by administering multiple doses of the MPV preparation.

Brucellosis

Brucellosis causes worldwide economic and public health problems. Brucellosis is caused by Brucella spp. It is adapted to many mammalian species, including man, domestic animals and a variety of wild animals. Six Brucella spp. cause brucellosis in animals; they are *B. abortus, B. canis, B. melitensis, B. neotomae, B. ovis* and *B. suis*. Both domestic and wild animals serve as reservoirs for potential spread of brucellosis to other animals and man.

Such infections cannot be cleared with antibiotics because the infectious organisms reside within the cells of the reticuloendothelial system and are highly resistant to bactericidal activities of antibiotics. The quantity of antibiotics required and the length of treatment result in either toxic effects on the animal or an unacceptable high concentration of the antibiotic in the tissues of the animal.

The examples which follow comprise incorporating an antibiotic into MPVs, and then administering the encapsulated active substance to the animals by inoculating the infected animals intraperitoneally.

Effectiveness of treatments using MPVs

In the following experiments, MPVs were prepared as described in Section 5.

Twenty adult female Swiss Webster mice were infected with *B. canis* ATCC 23365 (5×10$^6$ colony forming units, CFU) intraperitoneally (I.P.) and divided into 2 groups of 10 mice each. Seven days and 10 days post-inoculation with *B. canis*, groups were treated as follows: Group 1, designated controls, received no treatment; Group 2 received MPVs containing gentamicin (10 mg/kg body weight) in a total volume of 0.3 ml, I.P. On day 17 post-inoculation with *B. canis*, all animals were sacrificed and spleens removed aseptically. Spleens were homogenized and serially diluted onto brucella agar to determine the number of surviving *B. canis* in spleens after treatment. Results after 3 days incubation are shown in Table VII.

The results of the two-stage treatment regimens on *B. canis* infections in vivo presented in Table VII, demonstrate that in groups receiving MPV-entrapped gentamicin at a concentration of 10 mg/kg of body weight administered on days 7 and 10 post-inoculation all viable bacteria were eliminated from spleens of infected animals.

TABLE VII
EFFECTIVENESS OF MPVs CONTAINING GENTAMICIN ON KILLING OF *B. CANIS* IN VIVO AFTER TWO TREATMENTS[a]

| | Colony-Forming Units per Spleen[b] |
| --- | --- |
| Control | 2.20 ± 0.26 × 10$^4$ |
| MPVs[c] | 0 |

[a]Intraperitoneal injections, 10 mg/kg body weight, were spaced at 3 day intervals. Controls received no treatment.
[b]Surviving *B. canis* was determined as the number of CFU isolated per spleen and is expressed as the mean ± S.D. of 20 cultures.
[c]Egg phosphatidylcholine to gentamicin ratios were 100 mg lipid to 30 mg gentamicin.

EXAMPLE

Treatment of systemic infections

Effect of single treatment of *S. typhimurium* infection using MPV-entrapped antibiotics Ten adult female Swiss Webster mice were infected with *S. typhimurium* (O.D.$_{420}$ of 0.430) at approximately 5×10$^6$ CFU per mouse, I.P., and divided into 2 groups of 5 mice each. One day post-inoculation with S. typhimurium, groups were tested as follows: Group 1, designated controls, received no treatment; Group 2 received MPVs (prepared as described in section 5) containing nafcillin-gentamicin in a 1:1 ratio (100 mg/kg body weight) in a total volume of 0.3 ml I.P. (total dose 0.27 mg gentamicin per mouse in 0.3 ml and approximately 0.27 mg nafcillin per mouse based upon comparable entrapment efficiencies for nafcillin and gentamicin). The animals were observed over 14 days for survival.

The results of the treatment are as follows: of the controls, after 2 days post-inoculation 2 mice survived, after 3 days no survivors were left; of Group 2, all animals survived until day 9 post-inoculation when one animal died, no other animal died during the 14 day period post-inoculation.

The results shown in Table VIII demonstrate the clinical effectiveness of the MPV preparations. There were no survivors in both the control group and the groups treated with unentrapped antibiotics. However, 100% of the infected mice treated with gentamicin and nafcillin entrapped in MPVs survived.

TABLE VIII

EFFECT OF A SINGLE TREATMENT
OF S. TYPHIMURIUM INFECTED MICE
WITH FREE OR MPV-ENTRAPPED ANTIBIOTIC

| Day | Surviving Animals Group[a] | | |
|---|---|---|---|
| | 1 | 2 | 3 |
| 0 (infection) | 10 | 10 | 10 |
| 1 (treatment) | 10 | 10 | 10 |
| 2 | 3 | 6 | 10 |
| 3 | 2 | 5 | 10 |
| 4 | 0 | 1 | 10 |
| 5 | 0 | 1 | 10 |
| 6 | 0 | 0 | 10 |
| 7 | 0 | 0 | 10 |
| 8 | 0 | 0 | 10 |
| 9 | 0 | 0 | 10 |
| 14 | 0 | 0 | 10 |

[a]Thirty mice divided into 3 groups were infected with S. typhimurium. The groups were treated as follows: (1) control; (2) nafcillin/gentamicin; (3)MPVs containing nafcillin/gentamicin.

Effect of multiple treatment of S. tyhphimuriun infected mice with MPV-entrapped antibiotics Twenty adult female Swiss Webster mice were infected with S. typhimurium (O.D.$_{420}$ of 0.430 at approximately) $5.5 \times 10^6$ CFU, I.P., and divided into 2 groups of 10 mice each. One day post-infection and seven days post-infection groups were treated as follows: Group 1, designated controls, received no treatment; Group 2 received MPVs containing chloramphenicol (100 mg/kg body weight) in a total volume of 0.1 ml I.P. The animals were observed over the following 14 day period for survival.

The results shown in Table IX indicate that 90% of the infected animals treated with MPV-entrapped chloramphenicol survived whereas none of the untreated animals survived.

These results demonstrate the therapeutic effectiveness of treatment of systemic infections with antibiotic-entrapped MPVs.

TABLE IX

EFFECT OF MULTIPLE TREATMENT MICE
INFECTED WITH S. TYPHIMURIUM

| Day | Surviving Animals | | |
|---|---|---|---|
| | Controls | Free Chloramphenicol | MPV/ Chloramphenicol |
| 0 (infection) | 10 | 10 | 10 |
| 1 (treatment) | 10 | 10 | 10 |
| 2 | 3 | 9 | 10 |
| 3 | 3 | 6 | 10 |
| 4 | 0 | 4 | 10 |
| 5 | 0 | 4 | 10 |
| 6 | 0 | 1 | 10 |
| 7 (treatment) | 0 | 0 | 9 |

TABLE IX-continued

EFFECT OF MULTIPLE TREATMENT MICE
INFECTED WITH S. TYPHIMURIUM

| Day | Surviving Animals | | |
|---|---|---|---|
| | Controls | Free Chloramphenicol | MPV/ Chloramphenicol |
| 14 | 0 | 0 | 9 |

The preceding Examples are given for purposes of illustration and not by way of limitation on the scope of the invention.

What is claimed is:

1. A method for preparing lipid vesicles comprising:
   (a) forming a solution of an amphipathic lipid in at least one organic solvent plus a first aqueous component in amounts sufficient to form a monophase;
   (b) evaporating the organic solvent or solvents of the monophase at a temperature and pressure which maintains the monophase and facilitates evaporation until a film forms; and
   (c) adding a second aqueous component to the film and agitating the second aqueous component with the film in order to resuspend the film and to form lipid vesicles.

2. The method according to claim 1 in which the monophase is sonicated during evaporation.

3. The method according to claim 1 in which the monophase is vortexed during evaporation.

4. The method according to claim 1 in which the monophase is shaken by hand during evaporation.

5. The method according to claim 1 in which the monopase is rotoevaporated.

6. The method according to claim 1 in which at least one organic solvent comprises an alcohol.

7. The method according to claim 6 in which the alcohol comprises ethanol.

8. The method according to claim 6 in which the alcohol comprises 2-propanol.

9. The method according to claim 6 in which the alcohol comprises methanol.

10. The method according to claim 1 in which at least one organic solvent comprises acetone.

11. The method according to claim 1 in which at least one organic solvent comprises tetrahydrofuran.

12. The method according to claim 1 in which at least one organic solvent comprises glyme.

13. The method according to claim 1 in which at least one organic solvent comprises dioxane.

14. The method according to claim 1, in which at least one organic solvent comprises pyridine.

15. The method according to claim 1, in which at least one organic solvent comprises diglyme.

16. The method according to claim 1, in which at least one organic solvent comprises 1-methyl-2-pyrrolidone.

17. The method according to claim 1, in which at least one organic solvent comprises butanol-2.

18. The method according to claim 1, in which at least one organic solvent comprises butanol-1.

19. The method according to claim 1, in which at least one organic solvent comprises isoamyl alcohol.

20. The method according to claim 1, in which at least one organic solvent comprises isopropanol.

21. The method according to claim 1, in which at least one organic solvent comprises 2-methoxyethanol.

22. The method according to claim 1, in which at least one organic solvent comprises chloroform/methanol in a 1:1 ratio.

23. The method according to claim 7, in which the volume of organic solvent or solvents and the volume of the first aqueous component are in a ratio of about 25:1 to about 1:1.

24. The method according to claim 7, in which the amphipathic lipid comprises phosphatidylcholine.

25. The method according to claim 7, wherein the temperature at which the evaporation is performed is 54° C.

26. The method according to claim 1 in which the organic solvent or solvents contains an anti-oxidant.

27. The method according to claim 26, in which the anti-oxidant comprises butylated hydroxytoluene.

28. The method according to claim 27, in which the anti-oxidant comprises alpha-tocopherol.

29. The method according to claim 1, in which an agent to be entrapped in the lipid vesicles is added to the monophase before evaporation.

30. The method according to claim 1, in which an agent to be entrapped in the lipid vesicles is added to film with the second aqueous component.

31. The method according to claim 29 or 30, in which the agent to be entrapped comprises a biologically active agent.

32. The method according to claim 31, in which the biologically active agent comprises an antibacterial compound, an antifungal compound, an antiparasitic compound, or an antiviral compound.

33. The method according to claim 31, in which the biologically active agent comprises a tumoricidal compound, a toxin, a cell receptor binding molecule, or an globulin.

34. The method according to claim 31, in which the biologically active agent comprises an anti-inflammatory compound, an anti-glaucoma compound, a mydriatic compound, or a local anesthetic compound.

35. The method according to claim 31, in which the biologically active agent comprises an enzyme, a hormone, a neurotransmitter, an immunomodulator, a nucleotide or a cyclic adenosine monophosphate.

36. The method according to claim 31, in which the biologically active agent comprises a dye, a fluorescent compound, a radioactive compound, or a radio-opaque compound.

37. The method according to claim 31, in which the biologically active agent comprises an antibiotic.

38. The method according to claim 37, in which the antibiotic comprises an aminoglycoside antibiotic.

39. The method according to claim 38, in which the aminoglycoside antibiotic comprises gentamicin., 40. The method according to claim 37, in which the antibiotic comprises a penicillin.

41. The method according to claim 40, in which the penicillin comprises nafcillin.

42. The method according to claim 32, in which the antibiotic comprises a tetracycline.

43. The method according to claim 42, in which the tetracycline comprises doxycycline.

44. The method according to claim 37, in which the antibiotic comprises chloramphenicol.

45. Lipid vesicles produced by a method comprising:
(a) forming a solution of an amphipathic lipid in at one organic solvent plus a first aqueous component in amounts sufficient to form a monophase;
(b) evaporating the organic solvent or solvents of the monophase at a temperature and pressure which maintains the monophase and facilitates evaporation until a film forms;
(c) adding a second aqueous component to the film and agitating the second aqueous component with the film in order to resuspend the film and to form lipid vesicles.

46. Lipid vesicles according to claim 45, in which the major lipid component of the vesicles comprises phosphatidycholine.

47. Lipid vesicles according to claim 45, in which the major lipid component of the vesicles comprises egg phosphatidylcholine.

48. Lipid vesicles according to claim 45, in which an anti-oxidant comprises a component of the vesicle.

49. Lipid vesicles according to claim 48, in which the anti-oxidant comprises butylated hydroxytoluene.

50. Lipid vesicles according to claim 48, in which the anti-oxidant comprises alpha-tocopherol.

51. Lipid vesicles prepared according to the method of claim 45, in which a biologically active agent is entrapped within the vesicles.

52. Lipid vesicles according to claim 51, in which the biologically active agent was added to the monophase.

53. Lipid vesicles according to claim 51, in which the biologically active agent was added to the film with the second aqueous component.

54. Lipid vesicles according to claim 51, in which the bioogically avtice agent entrapped within the vesicles comprises an antibacterial compound, an antifungal compound, an antiparasitic compound, or an antiviral compound.

55. Lipid vesicles according to claim 51, in which the biologically active agent entrapped within the vesicles comprises a tumoricidal compound, a toxin, a cell receptor binding compound or an immunoglobulin.

56. Lipid vesicles according to claim 51, in which the biologically active agent entrapped within the vesicles comprises an anti-inflammatory compound, an anti-glaucoma compound, a mydriatic compound or a local anesthetic.

57. Lipid vesicles according to claim 51, in which the biologically active agent entrapped within the vesicles comprises an enzyme, a hormone, a neurotransmitter, an immunomodulator, a nucleotide or a cyclic adenosine monophosphate.

58. Lipid vesicles according to claim 51, in which the biologically active agent entrapped within the vesicles comprises a dye, a fluorescent compound, a radioactive compound, or a radio-opaque compound.

59. Lipid vesicles according to claim 51, in which the biologically active agent comprises an antibiotic.

60. Lipid vesicles according to claim 59, in which the antibiotic comprises an aminoglycoside antibiotic.

61. Lipid vesicles according to claim 60, in which the aminoglycoside antibiotic comprises gentamicin.

62. Lipid vesicles according to claim 59, in which the antibiotic comprises a penicillin.

63. Lipid vesicles according to claim 62, in which the penicillin comprises nafcillin.

64. Lipid vesicles according to claim 59, in which the antibiotic comprises a tetracycline.

65. Lipid vesicles according to claim 64, in which the tetracycline comprises doxycycline.

66. Lipid vesicles according to claim 59, in which the antibiotic comprises chloramphenicol.

67. A method for delivery of a biologically active agent in vivo comprising: administering to an organism the lipid vesicles of claim 51.

68. The method according to claim 67, in which the lipid vesicles are administered topically, intraperitoneally, intravenously, intramuscularly, intraarticularly, subcutaneously, intraauricularly or orally.

69. A method for treatment of infections in animals or plants, comprising: administering lipid vesicles of claim 45 containing a compound effect for treating the infection.

70. The method according to claim 69, in which the infection is intracellular.

71. the method according to claim 69, in which the infection is extracellular.

72. The method according to claim 69, in which the infection is caused by a parasite.

73. The method according to claim 69, in which the infection is caused by a bacteria.

74. The method according to claim 73, in which the bacteria comprises Brucella spp.

75. The method according to claim 74, in which the administration is intraperitoneal.

76. The method according to claim 73, in which the bacteria comprises Salmonella spp.

77. The method according to claim 76, in which the administration is intraperitoneal.

78. The method according to claim 69, in which the infection comprises an ocular infection.

79. The method according to claim 78, in which the administration is topical.

80. The method for the treatment of afflictions in animals or plants comprising: administering the lipid vesicles of claim 45 containing a compound effective for treating the affliction.

81. The method according to claim 80, in which the affliction comprises an ocular affliction.

82. The method according to claim 81, in which the ocular affliction comprises glaucoma.

83. The method according to claim 82, in which the administration is topical.

* * * * *